US008734860B2

(12) United States Patent
Sun

(10) Patent No.: US 8,734,860 B2
(45) Date of Patent: May 27, 2014

(54) TRADITIONAL CHINESE MEDICINAL OINTMENT FOR TREATING BURN, SCALD AND INFECTIVE TRAUMA AND PREPARATIVE METHOD THEREOF

(76) Inventor: Xinwei Sun, Jinan (CN)

( * ) Notice: Subject to any disclaimer, the term of this patent is extended or adjusted under 35 U.S.C. 154(b) by 293 days.

(21) Appl. No.: 13/259,617

(22) PCT Filed: Mar. 4, 2010

(86) PCT No.: PCT/CN2010/000259
§ 371 (c)(1),
(2), (4) Date: Sep. 23, 2011

(87) PCT Pub. No.: WO2010/111886
PCT Pub. Date: Oct. 7, 2010

(65) Prior Publication Data
US 2012/0015041 A1   Jan. 19, 2012

(30) Foreign Application Priority Data

Apr. 2, 2009  (CN) .......................... 2009 1 0020093

(51) Int. Cl.
*A61K 36/00* (2006.01)
*A61K 35/64* (2006.01)
*A61K 35/12* (2006.01)

(52) U.S. Cl.
USPC ............................ 424/725; 424/539; 424/537

(58) Field of Classification Search
USPC ......................................... 424/725, 539, 537
See application file for complete search history.

(56) References Cited

FOREIGN PATENT DOCUMENTS

CN  101513441 A  8/2009

OTHER PUBLICATIONS

Tsumura & Co., Tsumura Shiunko Ointment, record for product No. 875200, http://www.tsumura.co.jp/english/products/pi/JPR_T501.pdf, 2007.*
Murasakiso, *Lithospermum erythrorhizon*, sieb. et zucc., eine japanische Färbe- und Medizinalpflanze, http://www.weiterbildung.uzh.ch/programme/ethnobot/Abschlussarbeiten/MoehrAbschlussarbeitFinal.pdf, 2009.*
Science Papers: Chiefly Pharmacological and Botanical, D. Hanbury, J. Inca, ed., Macmillan and Co., London, 1876, p. 71.*
International Search Report issued in International Application No. PCT/CN2010/000259 on May 27, 2010 (with translation).
Written Opinion of the International Searching Authority issued in International Application No. PCT/CN2010/000259 on May 27, 2010 (with partial translation).

* cited by examiner

*Primary Examiner* — Rosanne Kosson
(74) *Attorney, Agent, or Firm* — Oliff PLC

(57) ABSTRACT

This invention is disclosing a pure ointment of traditional Chinese medicine which was invented to treat burn or scald, and infectious trauma, and its preparation. The ointment has solved a number of problems in the treatment of burn or scald, and infectious trauma, such as the high cost of current drugs, post-treatment scar, and unfavorable therapeutic effect. The advantages of this ointment include low cost, favorable therapeutic effect, short course, and without scar after treatment. Its formula is based on the weight of every five hundred portions of following ingredients: lithospermum, 4-10 portions, beeswax, 5-20 potions, insect-white wax, 5-20 portions, and lard, 450-486 portions.

6 Claims, No Drawings

TRADITIONAL CHINESE MEDICINAL OINTMENT FOR TREATING BURN, SCALD AND INFECTIVE TRAUMA AND PREPARATIVE METHOD THEREOF

TECHNICAL FIELD

This invention involved a kind of pure ointment of traditional Chinese medicine, which was invented for the treatment of burn or scald, and infectious trauma, and its preparation.

BACKGROUND TECHNOLOGY

Currently, it is extremely painful for patients with burn or scald which cost a lot of money during treatment. Unfortunately, these patients are hard to achieve ideal therapeutic effect even after spending substantial cost, and often with scars. Moreover, the process of treating scars during wound healing would bring agony to patients. For infectious trauma, such as would which is discharging pus, during treatment debridement is needed, which makes patients painful, and often with scars.

SUMMARY OF THE INVENTION

This invention aims to solve following problems, including the high cost of drugs for burn or scald, and infectious trauma, scarring after treatment, and unfavorable therapeutic effect, by providing a kind of pure ointment of traditional Chinese medicine for the treatment of burn or scald, and infectious trauma, which has advantages of low cost, favorable therapeutic effect, short course, and without scar after treatment, and its preparation For this purpose, this invention applied following technical protocols:

A kind of pure ointment of traditional Chinese medicine for the treatment of burn or scald, and infectious trauma, which is based on the weight of every five hundred portions of following ingredients: lithospermum, 4-10 portions, beeswax, 5-20 potions, insect-white wax, 5-20 portions, and lard, 450-486 portions.

It is based on the weight of every five hundred portions of following ingredients: lithospermum, 6 portions, beeswax, 8 potions, insect-white wax, 10 portions, and lard, 476 portions.

It is based on the weight of every five hundred portions of following ingredients: lithospermum, 8 portions, beeswax, 10 potions, insect-white wax, 15 portions, and lard, 467 portions.

Detailed Description of the Invention

The preparation of a pure ointment of traditional Chinese medicine for the treatment of burn or scald, and infectious trauma as follows: after lard is heated to 200-230° C., corresponding portions of lithospermum, beeswax and insect-white wax are added, respectively, then fully stirred the mixture. When beeswax and insect-white wax are melted, stop heating, and filtrate herbal residues while still hot, then the remaining is cooled down to room temperature.

Although this invention only contains four kinds of ingredients, each has significant therapeutic effect, because of elaborately designed compatibility and accurate doses. The ingredients are described as below, respectively.

Lithospermum, an ingredient with bitter, cold, properties, belongs to heart and liver meridian, and is mainly used to cool and activate blood, detoxify toxins, promote eruption and vesiculation. In addition, it can also treat hematemesis; hemorrhinia, hematuria, purpura, macule, measles, jaundice, carbuncle abscess, and burn (refer to Dictionary of Traditional Chinese Medicine, 2nd edition, page 3270-3273).

Beeswax, an ingredient with sweat, light, and smooth properties, belongs to spleen, stomach and large intestine meridian, and is mainly used to detoxify toxin, promote granulation and stop bleeding. Besides, it can also treat carbuncle abscess, ulcer, dysentery and metrostaxis of fetal movement (refer to Dictionary of Traditional Chinese Medicine, 2nd edition, page 3486-3487).

Insect-white wax, an ingredient with sweat, light, and warm properties, belongs to liver meridian, and is mainly used to stop bleeding, promote granulation and control pain. Moreover, it can also treat hemorrhage o incised wound, hematuria, hematochezia, and healing difficulty of ulcers (refer to Dictionary of Traditional Chinese Medicine, 2nd edition, page 1214-1215).

Lard, an ingredient with sweat and slightly cold properties, is mainly used to reinforce deficiency, moisturize dryness, and detoxify toxins. It can also treat consumptive diseases, constipation, skin chap, cough due to lung deficiency, malignant score, and scalds and burns (refer to Dictionary of Traditional Chinese Medicine, 2nd edition, page 3073-3074).

Through properly setting the proportion of each ingredient, this invention not only control the drug cost, but also ensure the efficacy. Furthermore, respective property of each drug is fully considered during collocation, thus favorable therapeutic effect is guaranteed.

Administration: Smear the drug evenly in sterile medicinal cotton, which covers the wound. If the wood is too large, multiple medicinal cotton should be used to cover the whole wound evenly, then bind up and fix medicinal cotton with gauze. After above process, a patient could dress and cover quilt. The bind up with gauze must not be too tight, to avoid wound healing. Outside the gauze, it should not use air proof material, such as plastic cloth, to bind up. Based on the damage degree of wound and drug absorption, dressing change is done every 24/12/6 hours.

Efficacy: This drug, a red semisolid ointment, is used to combat bacteria and inflammation, activate and cool blood, eliminate swelling, control pain, and remove the necrotic tissue, promote granulation, and facilitate skin growth, thus make it a ideal drug for burn or scald, and infectious trauma.

Characteristics of the Drug

1. The time between administration and work is short: 2-3 minutes after administration, the drug works rapidly to control pain;
2. Favorable permeability: The drug could penetrate rapidly to below the wound, to promote tissue restoration, and make the necrotic tissue liquefied and discharged.
3. Potent anti-infection effect: This drug can combat bacteria and inflammation without sterile condition, and have favorable effect on infective wounds with pus.
4. Soften wounds and keep humidification: The drug can soften dry, hard crusted wounds and remove crust after it fully permeates to wounds, to maintain wound humid and promote wound healing.
5. Accelerated wound healing: The drug would form a protective layer on the wound, which is helpful for wound healing, and without scars after complete healing.
6. Easy to use: Smear the drug in sterile medicinal cotton, which covers the wound. After above process, a patient could dress and cover quilt, which means exposure therapy is unnecessary.

Cases Presentation

This drug has been applied to hundreds of patients, with significant efficacy. Some cases were listed as below.

I, Burns

An old woman in her sixties presented to a hospital with burns in hands, feet and legs caused by outbreak of a fire on gas burner. During several days in hospital, he had a fever, and used antibiotics through persistent intravenous drip, but with poor effect. He was introduced to our hospital. At admission, the wound was black with dry, hard crust, below which there was pus. The wounded limbs were swelling and painful. The drug was applied, and dressing change was done every 24 hours. Crusts (3-4 millimeters thick) were soften and fell off the wound gradually, and totally fell off after 3 days. At that time, the wound with substantial pus was exposed. Subsequently, the wound was cleaned, and the drug is continued for 2 weeks. At the end of treatment, the wound completely healed, the skin was red and smooth without scar.

A man in his forties whose chest and hands were burned by gasoline was introduced to us. On examination, the epidermis on the wound totally fell off, and the wound was red, swelling and painful. The drug was applied, and dressing change was done every 12 hours. The wound was cured after 10 days without scar.

II, Oil Scald

A male construction worker in his thirties lost his balance by accident during boiling asphalt. His hands had pressed asphalt, and severely scalded. The asphalt was stripped in hospital. After more than 10 days treatment, the effect was poor. He was introduced to us. This drug was applied, and dressing change was done every 12 hours. The wound recovered after 2 weeks without scar.

A woman in her forties whose face, chest and arms were scalded by hot oil during frying dough sticks, came to us. The epidermis on the wound partly fell off, and the wound was red, swelling and painful. This drug was applied, and dressing change was done every 12 hours. The wound recovered after 10 days without scar.

III, Scalded by Boiled Water

A one-year old little boy was scalded by boiled water. He was treated a week in an ulcer. The hospital suggested amputation, which was refused by the infant's parents. He was introduced to us. His pain was controlled immediately after using our drug, and his did not cried. Dressing change was done every 12 hours. The wound recovered after a dozen of days without scar.

A five years old girl knocks over a tub with boiled water by accident. The water poured to her head, causing her face swollen. The epidermis fell off, and she felt intensive pain. She was sent to us immediately. This drug was applied, and she did not cry any more. The dressing change was done every 12 hours. The wound recovered after one week without scar.

IV, Infectious Trauma

A woman in her fifties scratched her instep by accident during doing farm work with a grappler, and formed a penetrating wound. Later, the wound was infective and discharged pus, with swelling and ulcer aggravating. She received antibiotics infusion in a country clinic for more than 10 days, but achieved poor efficacy. So she came to us. This drug was applied, and the dressing change was done every 12 hours. After one week; her swelling and pus resolved. Another 4-5 days later, she recovered completely without scar.

An old man in his seventies developed ischemic necrotic suppuration in buttock, and erosive ulcer, with coccyx exposed, due to long term in bed in a hospital. The therapeutic effect was unfavorable, with ulcer not healing for a long time. His son brought him to us. This drug was used, and the dressing change was done every 24 hours. The wound healed after more than one month without scar.

Specific Mode of Execution

The invention is further described with following examples:

EXAMPLE 1

A kind of pure ointment of traditional Chinese medicine for the treatment of burn or scald, and infectious trauma, which is based on the weight of every five hundred portions of following ingredients: lithospermum, 4 portions, beeswax, 5 potions, insect-white wax, 5 portions, and lard, 486 portions.

The preparation as follows: after lard is heated to 200° C., corresponding portions of lithospermum, beeswax and insect-white wax are added, respectively, then fully stirred the mixture. When beeswax and insect-white wax are melted, stop heating, andfiltrate herbal residues while still hot, then the remaining is cooled down to room temperature.

EXAMPLE 2

A kind of pure ointment of traditional Chinese medicine for the treatment of burn or scald, and infectious trauma, which is based on the weight of every five hundred portions of following ingredients: lithospermum, 6 portions, beeswax, 8 potions, insect-white wax, 10 portions, and lard, 476 portions.

The preparation as follows: after lard is heated to 210° C., corresponding portions of lithospermum, beeswax and insect-white wax are added, respectively, then fully stirred the mixture. When beeswax and insect-white wax are melted, stop heating, andfiltrate herbal residues while still hot, then the remaining is cooled down to room temperature.

EXAMPLE 3

A kind of pure ointment of traditional Chinese medicine for the treatment of burn or scald, and infectious trauma, which is based on the weight of every five hundred portions of following ingredients: lithospermum, 8 portions, beeswax, 10 potions, insect-white wax, 15 portions, and lard, 467 portions.

The preparation as follows: after lard is heated to 220° C., corresponding portions of lithospermum, beeswax and insect-white wax are added, respectively, then fully stirred the mixture. When beeswax and insect-white wax are melted, stop heating, and filtrate herbal residues while still hot, then the remaining are cooled down to room temperature.

EXAMPLE 4

A kind of pure ointment of traditional Chinese medicine for the treatment of burn or scald, and infectious trauma, which is based on the weight of every five hundred portions of following ingredients: lithospermum, 10 portions, beeswax, 20 potions, insect-white wax, 20 portions, and lard, 467 portions.

The preparation as follows: after lard is heated to 230° C., corresponding portions of lithospermum, beeswax and insect-white wax are added, respectively, then fully stirred the mixture. When beeswax and insect-white wax are melted, stop heating, andfiltrate herbal residues while still hot, then the remaining is cooled down to room temperature.

The invention claimed is:

1. An ointment for the treatment of a patient's skin conditions, comprising 4 to 10 parts by weight lithospermum, 5 to 20 parts by weight beeswax, 5 to 20 parts by weight insect-white wax, and 450 to 486 parts by weight lard, based on five hundred parts by weight of the lithospermum, beeswax, insect-white wax, and lard.

2. The ointment as described in claim 1, comprising 6 parts by weight lithospermum, 8 parts by weight beeswax, 10 parts by weight insect-white wax, and 476 parts by weight lard, based on five hundred parts by weight of the lithospermum, beeswax, insect-white wax, and lard.

3. The ointment as described in claim 1, comprising 8 parts by weight lithospermum, 10 parts by weight beeswax, 15 parts by weight insect-white wax, and 467 parts by weight lard, based on five hundred parts by weight of the lithospermum, beeswax, insect-white wax, and lard.

4. A method for preparing the ointment as described in claim 1, comprising:
   a) heating the lard to 200-230° C,
   b) adding the lithospermum, beewax and insect-white wax to the heated lard to form a mixture, wherein the amounts added yield the amounts of claim 1,
   c) stirring the mixture,
   d) after the beewax and insect-white wax are melted, stopping heating,
   e) filtering the mixture while the mixture is still hot, and
   f) cooling the mixture to room temperature.

5. The ointment as described in claim 1, wherein the skin conditions include burns and scalding.

6. The ointment as described in claim 1, wherein the skin conditions include infectious trauma.

* * * * *